(12) United States Patent
Rao et al.

(10) Patent No.: US 7,285,669 B2
(45) Date of Patent: Oct. 23, 2007

(54) PROCESS FOR PREPARING 2,6-DIAMINO-4,5,6,7-TETRAHYDRO-BENZOTHIAZOLE

(75) Inventors: Dharmaraj Ramachandra Rao, Maharashtra (IN); Rajendra Narayanrao Kankan, Maharashtra (IN)

(73) Assignee: Cipla Limited, Mumbai Central, Mumbai (IN)

( * ) Notice: Subject to any disclaimer, the term of this patent is extended or adjusted under 35 U.S.C. 154(b) by 0 days.

(21) Appl. No.: 10/533,637

(22) PCT Filed: Nov. 3, 2003

(86) PCT No.: PCT/GB03/04734

§ 371 (c)(1),
(2), (4) Date: Nov. 29, 2005

(87) PCT Pub. No.: WO2004/041797

PCT Pub. Date: May 21, 2004

(65) Prior Publication Data

US 2006/0100256 A1    May 11, 2006

(30) Foreign Application Priority Data

Nov. 4, 2002  (GB) ................................ 0225701.2

(51) Int. Cl.
*C07D 277/82*  (2006.01)
*A61K 31/136*  (2006.01)

(52) U.S. Cl. ...................................... 548/164; 514/367
(58) Field of Classification Search ................. 548/164
See application file for complete search history.

(56) References Cited

OTHER PUBLICATIONS

Schneider, et al. Dopamine Autoreceptor Agonists: Resolution and Pharmacological Activity of 2,6-Diaminotetrahydrobenzothiazole and an Aminothiazole Analogue of Apomorphine. J. Med. Chem. 1987, 30, 494-498.*
Janet Allinger and Norman L. Allinger; "The Conformers of 2-Bromocyclohexanone" XP-002253277; Tetrahedron, 1958, vol. 2, pp. 64-74 Pergamon Press Ltd., London.

* cited by examiner

*Primary Examiner*—Rebecca Anderson
*Assistant Examiner*—Shawquia Young
(74) *Attorney, Agent, or Firm*—Stevens, Davis, Miller & Mosher, LLP

(57) ABSTRACT

2,6-diamino-4,5,6,7-tetrahydro-benzothiazole, which is useful for making pramipexole, is made by: (i) reacting bromine with a solution of 4-acetamido-cyclohexanone in water to produce 2-bromo-4-acetamido-cyclohexanone; (ii) after step (i), adding thiourea to produce 6-acetyl amino-2-amino-4,5,6,7-tetrahydro-benzthiazole; (iii) after step (ii), adding an aqueous solution of hydrobromic acid to produce 2,6-diamino-4,5,6,7-tetrahydro-benzthiazole dihydrobromide; and (iv) after step (iii), isolating 2,6-diamino-4,5,6,7-tetrahydro-benzthiazole.

18 Claims, No Drawings

PROCESS FOR PREPARING 2,6-DIAMINO-4,5,6,7-TETRAHYDRO-BENZOTHIAZOLE

This application is a 35 U.S.C. §371 U.S. National Stage Application of International Application No. PCT/GB2003/004734, filed on Nov. 3, 2003, claiming the priority of Great Britain Application No. 0225701.2, filed Nov. 4, 2002, the entire disclosures of which are incorporated herein by reference in their entireties.

This invention relates to a process for making 2,6-diamino-4,5,6,7-tetrahydro-benzthiazole, an intermediate useful in the production of pramipexole. The invention also relates to the synthesis of pramipexole.

(S)-4,5,6,7-tetrahydro-N6-propyl-2,6-benzothiazolediamine (or (S)-2-amino-4,5,6,7-tetrahydro-6-(propylamino)benzothiazole), more commonly known as pramipexole, is used in both early and late Parkinson's disease as a dopamine agonist, to stimulate dopamine receptors in the brain. This has been described in EP 0 186 087.

EP 0 186 087 also describes the synthesis of various tetrahydro benzothiazoles, including pramipexole. In particular, the synthesis of pramipexole by the following reaction pathway is described. An initial reaction between bromine and 4-acetylamido-cyclohexanone is carried out in glacial acetic acid, with stirring for several hours, at room temperature. This is followed by the addition of thiourea under refluxing conditions. The reaction mixture is cooled, and crystals of 6-acetylamino-2-amino-4,5,6,7-tetrahydro-benzthiazole-hydrobromide are precipitated. The precipitate is filtered, then washed with water and acetone. The crystals are then dissolved in hydrobromic acid and the solution is refluxed for several hours. The solution is then concentrated by evaporation and the residue dissolved in methanol, from which crystals of 2,6-diamino-4,5,6,7-tetrahydro-benzthiazole-dihydrobromide are formed. Subsequently, the 2,6-diamino-4,5,6,7-tetrahydro-benzthiazole-dihydrobromide may be converted to pramixexole.

This synthesis is illustrated by the following reaction scheme:

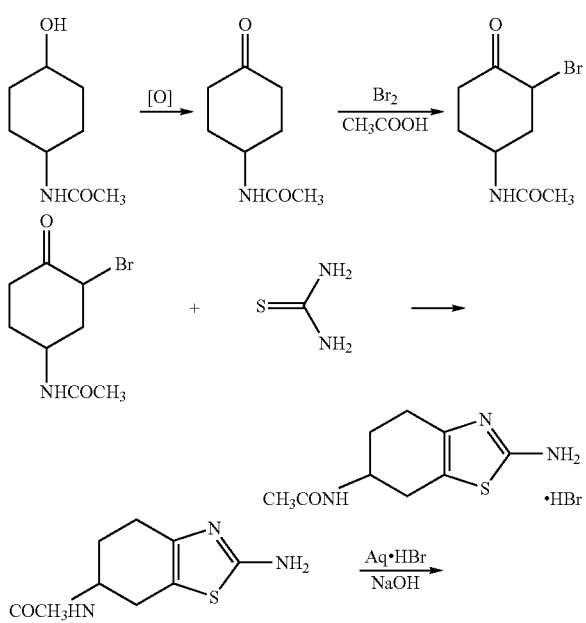

-continued

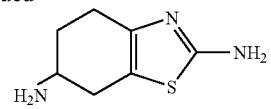

This synthetic pathway involves separate reaction steps, each requiring different conditions, solvents, temperatures, etc. This necessitates a discontinuous process and more than one isolation step, which entails longer processing time, lower yields (product is lost during each isolation step), increased effluent load and increased solvent usage, in comparison with a continuous process.

We have now found a way of synthesising 2,6-diamino-4,5,6,7-tetrahydro-benzthiazole from 4-acetamido-cyclohexanone, which avoids the multiple isolation steps used in the previously described processes.

According to one aspect of the present invention there is provided a method of synthesising 2,6-diamino-4,5,6,7-tetrahydro-benzothiazole, which method comprises comprising: (i) reacting bromine with a solution of 4-acetamido-cyclohexanone in water to produce 2-bromo-4-acetamido-cyclohexanone; (ii) after step (i), adding thiourea to produce 6-acetylamino-2-amino4,5,6,7-tetrahydro-benzthiazole-dihydrobromide; (iii) after step (ii), adding an aqueous solution of hydrobromic acid to produce 2,6-diamino-4,5,6,7-tetrahydro-benzthiazole; and (iv) after step (iii), isolating 2,6-diamino-4,5,6,7-tetrahydro-benzthiazole free base.

It is an important feature of the present invention that step (iii) is carried out without any isolation of the 6-acetylamino-2-amino-4,5,6,7-tetrahydro-benzthiazole produced in step (ii). Thus the entire synthesis can be carried out in a single reaction vessel. Preferably at least three successive steps of steps (i) to (iv) are carried out in a single reaction vessel.

Prior to step (i), the method may comprise the step of oxidising 4-acetamido-cyclohexanol to produce 4-acetamido-cyclohexanone. This step may be carried out in the same reaction vessel as subsequent steps (i) to (iv), thereby avoiding an additional isolation step.

The oxidation reaction may be carried out using oxidising agents including, for example, Jones reagent, sodium hypochlorite, manganese dioxide, pyridinium dichromate or potassium permanganate.

In step (i), the 4-acetamido-cyclohexanone solution and the bromine are preferably combined in the reaction vessel at a temperature in the range 5° C. to 75° C., more preferably in the range 15° C. to 40° C., and roost preferably about room temperature (approximately 25° C.). The bromine is preferably added dropwise to the 4-acetamido-cyclohexanone solution. After the bromine and the 4-acetamido-cyclohexanone solution have been combined, the mixture is preferably heated to a temperature in the range 30° C. to 80° C., more preferably 40° C. to 50° C., and most preferably about 45° C., and maintained at or near this temperature until the bromination is complete. The completion of bromination is indicated by the elimination of the characteristic brown colour of the bromine.

In step (ii), the temperature is preferably increased to 50° C. to 95° C., more preferably to 70° C. to 90° C., and most preferably to about 80° C.

In step (iii), the reaction mixture is preferably refluxed.

In step (iv), the reaction mixture is preferably cooled to 1° C. to 35° C., more preferably to 5° C. to 20° C., and most preferably to about 10° C., and the mixture is then neutralised. Typically the neutralisation is carried out with caustic lye solution (NaOH), although other alkalis may be used Following neutralisation, the product, 2,6-diamino-4,5,6,7-tetrahydro-benzthiazole, is isolated. The isolation may be carried out by filtration, centrifugation or any other suitable means. Following isolation, the product is preferably washed with chilled water.

The starting compound, 4-acetamido-cyclohexanone, may conveniently be formed by the oxidation of 4-acetamido-cyclohexanol.

The above described compound, 2,6-diamino-4,5,6,7-tetrahydro-benzthiazole, is useful as an intermediate in the production of pramipexole and related compounds.

According to another aspect of the present invention there is provided a method of synthesising pramipexole, comprising the steps of: forming 2,6-diamino-4,5,6,7-tetrahydro-benzothiazole by the method of the present invention, then converting it to pramipexole.

The conversion of 2,6-diamino-4,5,6,7-tetrahydro-benzothiazole to pramipexole is well known in the prior art and is described, for example, in U.S. Pat. No. 4,731,374. Any of the methods described in U.S. Pat. No. 4,731,374, may be used in the present invention.

In one embodiment, the 2,6-diamino-4,5,6,7-tetrahydro-benzothiazole is converted to pramipexole by reaction with a propionyl halide, such as propionyl bromide, under suitable reaction conditions.

Both 2,6-diamino-4,5,6,7-tetrahydro-benzthiazole and pramipexole have an asymmetric carbon atom, and exist as two distinct enantiomers: the S(−) isomer and the R(+) isomer. The pharmacological activity of the S(−) isomer of pramipexole is, however, twice as high as that of the R(+) isomer, and the name pramipexole is commonly used to refer to the optically pure S(−) form. In this specification, "2,6-diamino-4,5,6,7-tetrahydro-benzthiazole" encompasses the R(−) and S(−) enantiomers individually and also encompasses any mixture thereof including the racemic mixture, and the term "pramipexole" encompasses the R(+) and S(−) enantiomers individually and also the racemic mixture.

The resolution of a racemic mixture of 2,6-diamino-4,5, 6,7-tetrahydro-benzthiazole can be carried out after step (iv) above. Methods of resolution are known in the art. Alternatively, pramipexole racemate can be produced prior to resolution, then the mixture resolved, if desired.

The resolution of pramipexole racemate is described by Schneider and Mierau (J. Med. Chem. 30, 494 (1987)). This method uses the di-amino derivative of (±)-4,5,6,7-tetrahydro-N6-propyl-2,6-benzothiazolediamine as a substrate and L(+) tartaric acid as a resolution agent. Following resolution, optically active pramipexole has been prepared by two-step propylation of the single enantiomer of the di-amino precursor comprising the steps of reaction with propionanhydride followed by a reduction of the propionyl intermediate.

The synthesis of the present invention avoids the need to isolate intermediate compounds, and thus the yield is higher and the processing time is lower. Furthermore, owing to the absence of an organic solvent (such as acetic acid) the costs are lower, and the reaction conditions are milder—the milder reaction conditions also have a positive impact on product purity.

The invention will now be further described with reference to the following Examples.

EXAMPLE 1

Bromine (112 g) was added dropwise to a solution of 4-acetamidocyclohexanone (100 g) in 500 ml water at room temperature. The mixture was warmed to approximately 45° C. and maintained at this temperature until the bromine colour had been lost. To this, thiourea (125 g) was added, and the mixture was heated to approximately 80° C. To this, aqueous hydrobromic acid (100 ml) was added, and the contents of the reaction vessel were refluxed. The contents were then cooled to approximately 10° C., and neutralized with caustic lye solution. The product, 2,6-diamino-4,5,6,7-tetrahydro-benzthiazole, was isolated by filtration, and washed with chilled water and dried. The product was off-white in colour, and the yield was approximately 60 g in weight.

EXAMPLE 2

To a solution of 4-acetamido-cyclohexanol (100 g) in acetone (1 L) was added Jones reagent (prepared from 68.5 g chromic oxide, 105 g sulphuric acid and 400 ml water) at 10-15° C. The excess solvent was removed under reduced pressure. Ethyl acetate (600 ml) was added, the contents stirred for 10 minutes and the lower aqueous portion drained off. Ethyl acetate was concentrated under reduced pressure and the residue dissolved in water (500 ml). Bromine (112 g) was added dropwise and the further reactions were carried out as described in Example 1.

EXAMPLE 3

To a suspension of 4-acetamido-cyclohexanol (100 g) in water (300 ml) was added a solution of 10% sodium hypochlorite (500 ml) and the contents stirred at room temperature for 12 hours. To this was added liquid bromine (112 g) and further reactions carried out as described in Example 1.

It will be appreciated that the invention described above may be modified.

The invention claimed is:

1. A method of making 2,6-diamino-4,5,6,7-tetrahydro-benzothiazole, which method comprises the steps in sequence of: (i) reacting bromine with a solution of 4-acetamido-cyclohexanone in water to produce 2-bromo-4-acetamido-cyclohexanone; (ii) adding thiourea to produce 6-acetylamino-2-amino-4,5,6,7-tetrahydro-benzothiazole;
(iii) adding an aqueous solution of hydrobromic acid to produce 2,6-diamino-4,5,6,7-tetrahydro-benzothiazole; and
(iv) isolating 2,6-diamino-4,5,6,7-tetrahydro-benzothiazole.

2. A method according to claim 1, wherein step (iii) is carried out without isolating the 6-acetylamino-2-amino-4, 5,6,7-tetrahydro-benzothiazole produced in step (ii).

3. A method according to claim 1, wherein any three successive steps of steps (i) to (iv) are carried out in a single reaction vessel.

4. A method according to claim 1, wherein steps (i) to (iv) are carried out in a single reaction vessel.

5. A method according to claim 1, further comprising, prior to step (i), the step of oxidizing 4-acetamido-cyclohexanol to produce 4-acetamido-cyclohexanone.

6. A method according to claim 5, wherein the step of oxidizing 4-acetamido-cyclohexanol to produce 4-acetamido-cyclohexanone and at least three successive steps of steps (i) to (iv) are carried out in a single reaction vessel.

7. A method according to claim 1, wherein in step (i) the solution of 4-acetamido-cyclohexanone in water and bromine are combined at a temperature of from 15° C. to 40° C.

8. A method according to claim 1, wherein, after the bromine and the 4-acetamido-cyclohexanone solution have been combined, the mixture is heated to a temperature of from 40° C. to 50°0 C., and maintained at or near this temperature until the bromination is complete.

9. A method according to claim 1, wherein, in step (ii), the temperature is increased to 70° C. to 90° C.

10. A method according to claim 1, wherein step (iii) is carried out under refluxing conditions.

11. A method according to claim 1, wherein, after step (iii) but before step (iv), the reaction mixture is cooled to 5° C. to 20° C., then neutralized.

12. A method according to claim 1, further comprising the step of resolving the 2,6-diamino-4,5,6,7-tetrahydro-benzothiazole isolated in step (iv) into its R(+) and S(−) enantiomers and recovering the R(+) and/or S(−) enantiomer.

13. A method of synthesizing pramipexole, comprising the steps of: forming 2,6-diamino-4,5,6,7-tetrahydro-benzothiazole by a method according to claim 1, and converting it to pramipexole.

14. A method according to claim 13, wherein 2,6-diamino-4,5,6,7-tetrahydro-benzothiazole is converted to pramipexole by reaction with a propionyl halide.

15. A method according to claim 13, wherein the 2,6-diamino-4,5,6,7-tetrahydro-benzothiazole comprises the R(+) enantiomer.

16. A method according to claim 13, wherein the 2,6-diamino-4,5,6,7-tetrahydro-benzothiazole comprises the S(−) enantiomer.

17. A method according to claim 13, wherein the 2,6-diamino-4,5,6,7-tetrahydro-benzothiazole comprises a racemic mixture.

18. A method according to claim 14, further comprising the step of resolving the pramipexole into its R(+) and S(−) enantiomers and recovering the R(+) and/or S(−) enantiomer.

* * * * *